United States Patent [19]

Berrod et al.

[11] Patent Number: 5,312,981
[45] Date of Patent: May 17, 1994

[54] HYDROLYSIS OF ALKYL DICARBOXYLATES

[75] Inventors: Gerard Berrod, Villeurbanne; Eric Grillon, Armes; Francois Klinger, Chaponost, all of France

[73] Assignee: Rhone-Poulenc Chimie, Courbevoie, France

[21] Appl. No.: 63,679

[22] Filed: May 20, 1993

[30] Foreign Application Priority Data

May 20, 1992 [FR] France .................. 92 06392

[51] Int. Cl.$^5$ .............................. C07C 51/42
[52] U.S. Cl. .................................. 562/590
[58] Field of Search .......................... 562/590

[56] References Cited

U.S. PATENT DOCUMENTS

| | | | |
|---|---|---|---|
| 2,719,166 | 9/1955 | Robertson et al. | 260/452 |
| 4,754,064 | 6/1988 | Lillwitz | 562/509 |
| 4,965,201 | 10/1990 | Casey et al. | 435/134 |
| 5,143,834 | 9/1992 | Glassner et al. | 562/590 X |
| 5,168,055 | 12/1992 | Datta et al. | 435/145 |

FOREIGN PATENT DOCUMENTS 0134099  3/1985  European Pat. Off. .
1155780 10/1963  Fed. Rep. of Germany .

*Primary Examiner*—Arthur C. Prescott
*Attorney, Agent, or Firm*—Burns, Doane, Swecker & Mathis

[57] ABSTRACT

Dicarboxylic acids, e.g., adipic acid, are prepared by reactively distilling and hydrolyzing admixture of a $C_1$–$C_4$ alkyl aliphatic dicarboxylate and water, e.g., dimethyl adipate/water admixture, in liquid phase, in a distillation column, the lower end of which distillation column being charged with a gel of a crosslinked styrene/divinylbenzene resin bearing sulfonic acid substituents, the amount by weight of divinylbenzene comprising such resin ranging from 1% to 12% based on the total weight thereof and such resin having an exchange capacity of from 3 to 6.5 milliequivalents $H^+$/gram of dry resin, and including introducing the dicarboxylate/water admixture into the middle region of the column, withdrawing dicarboxylic acid from the base thereof and overhead distilling the alcohol of hydrolysis.

14 Claims, No Drawings

HYDROLYSIS OF ALKYL DICARBOXYLATES

BACKGROUND OF THE INVENTION

1. Field of the Invention

The present invention relates to the hydrolysis of lower alkyl dicarboxylates, the alkyl moieties of which having from 1 to 4 carbon atoms, into dicarboxylic acids.

2. Description of the Prior Art

Very generally in this art, the hydrolysis of esters is carried out in homogeneous medium either using an acid or using a base.

The use of a base leads to the formation of metal salts with the obvious disadvantages thereof.

The acidic hydrolysis of adipates presents the problem of the two-phase nature of the medium, due to the very low miscibility of water and the adipate. This is the reason it has been recommended to use mixtures of solvents (see, for example, *Journal of Indian Chemical Society*, 48(9), pages 811-2), which markedly complicates the subsequent separation and purification of the adipic acid obtained. Additionally, the use of a liquid acid presents significant problems of corrosion of the apparatus.

It has also been proposed to carry out the hydrolysis of adipates in heterogeneous medium on acidic resins.

Thus, an article published in *Synthetic Communications*, 19, pages 627-631 (1989) describes the hydrolysis of dimethyl adipate in an aqueous suspension of Dowex-50 resin at reflux. This type of suspension reaction does not solve the problem of displacement of the equilibrium of the reaction by removal of the methanol formed.

EP-A-0,056,489 proposes a solution to this problem, and describes a continuous process of hydrolysis, by water, of alkyl adipates containing 1 to 4 carbon atoms, at high temperature and in the presence of strongly acidic ion-exchange resin. The principal characteristics of this process is withdrawing part of the water/adipate reaction mixture on several plates of the column, below the region of delivery of this mixture into the column, the part thus removed is then passed onto a strongly acidic ion exchanger and is then recycled. Adipic acid is thus obtained at the base of the column, whereas alcohol/water mixtures are removed at the column head.

This '489 process requires the addition of a number of circuits to the column to ensure that the hydrolysis reaction proper is carried out, and its implementation is thus complex.

SUMMARY OF THE INVENTION

Accordingly, a major object of the present invention is the provision of a simplified, but very efficient process for the preparation of dicarboxylic acids by hydrolysis of alkyl dicarboxylates, in which the alkyl moieties contain 1 to 4 carbon atoms, employing a judiciously selected acidic resin.

Another object of this invention is the provision of an improved process for the preparation of dicarboxylic acids permitting both hydrolysis of the dicarboxylate, as well as separation of the alcohol formed.

Briefly, the present invention features a process for the preparation of a dicarboxylic acid by hydrolysis, in the liquid phase, of a $C_1$-$C_4$ alkyl aliphatic dicarboxylate, comprising subjecting a mixture of said dialkyl dicarboxylate and water to a reactive distillation by introducing said mixture into the middle section of a column charged with a gel-type resin containing sulfonic acid groups, secured in place by means of a support and having the following characteristics:

(a) a skeleton based on styrene and divinylbenzene, the amount of divinylbenzene by weight with respect to the total weight of said skeleton ranging from 1% to 12% and preferably from 2% to 5%, and (b) an exchange capacity of 3 to 6.5 milliequivalents $H^+$/gram of dry resin, and continuously distilling the alcohol formed by the hydrolysis reaction.

DETAILED DESCRIPTION OF PREFERRED EMBODIMENTS OF THE INVENTION

More particularly according to the present invention, gel-type resin containing sulfonic acid groups and having the following characteristics are the preferred:

(a) a skeleton or 3D network based on styrene and divinylbenzene, the amount of divinylbenzene by weight with respect to the total weight of said skeleton ranging from 1% to 12% and preferably from 2% to 5%, (b) an exchange capacity of 5 to 6.5 milliequivalents $H^+$/gram of dry resin, and (c) a mean particle size ranging from 100 to 2000 micrometers and preferably from 200 to 1200 micrometers.

Generally, the column used comprises a lower section in which the resin is arranged and whereat hydrolysis is carried out and an upper section, optionally containing a conventional packing, in which purification of the methanol is carried out.

The gel-type resins containing sulfonic acid groups are resins per se known to this art.

These are typically commercial resins/gels having the characteristics indicated above.

The resin/gel can be arranged in the column according to any one of a number of different techniques. It can be maintained in a metal, textile, ceramic or plastic structure ensuring an efficient liquid/solid and liquid/vapor exchange, the structure containing the resin being introduced into the column.

It can also be deposited or coated onto such a structure.

The resin/gel can also be placed onto capacitive plates.

The aforesaid alternatives are exemplary only.

The $C_1$ to $C_4$ alkyl aliphatic dicarboxylates hydrolyzed in the process of the invention are essentially the $C_1$ to $C_4$ alkyl esters of aliphatic dicarboxylic acids having 3 to 6 carbon atoms, such as, for example, the methyl, ethyl or n-propyl esters of succinic, ethylsuccinic, glutaric, methylglutaric, adipic, 2-hexenedioic or 3-hexenedioic acid.

Among these esters, dimethyl adipate, dimethyl methylglutarate, dimethyl ethylsuccinate and the dimethyl hexenedioates are the most commercially important. Dimethyl adipate is the compound whose hydrolysis is even more particularly important.

These esters and more specifically dimethyl adipate can be used either alone or in admixture.

In the description which follows, reference to the hydrolysis of dimethyl adipate should be considered as being generically applicable to another alkyl dicarboxylate as defined above.

Dimethyl adipate and water are introduced into the column in the middle section thereof, above the section where the resin/gel is situated.

The amount of water is such that the water/dimethyl adipate molar ratio is at least equal to 2.

Preferably, the amount of water will be in excess with respect to the stoichiometric amount, namely, the water/dimethyl adipate molar ratio will be greater than 2, generally ranging from 5 to 60.

The dimethyl adipate and water can be introduced separately, or as a mixture.

The hydrolysis of dimethyl adipate is carried out on the resin/gel and there is recovered, on the one hand, at the upper end of the column, the methanol formed and, on the other, at the lower end of the column, the adipic acid, the excess water, possibly unhydrolyzed monomethyl adipate and possibly unhydrolyzed dimethyl adipate.

The temperature in the column generally ranges from 80° C. to 150° C. in the part where the hydrolysis reaction is carried out and preferably ranges from 90° C. to 130° C.

The adipic acid prepared by the process according to the invention is separated from the water and other minor compounds which it may contain by the usual separation methods, for example by crystallization, especially by crystallization under vacuum.

The mother liquors generally contain from 2% to 10% of adipic acid and the various impurities or by-products of the reaction are advantageously recycled to the hydrolysis column.

In order to further illustrate the present invention and the advantages thereof, the following specific examples are given, it being understood that same are intended only as illustrative and in nowise limitative.

In said examples to follow, the "productivity of hydrolysis" is expressed in kg of adipic acid per kg of dry resin/gel per hour.

EXAMPLES

The apparatus used for the various examples and comparative tests included a column having an internal diameter of 4 cm, composed of two sections:

(a) a lower section having a length of 45 cm, in which the resin was arranged, hereinafter designated the "reactive" section, and (b) an upper section having a length of 150 cm, containing a standard packing permitting water/methanol separation.

This column was equipped with a distillation flask at its base, with a condenser at the head and with a reflux device; the reagents were introduced at the top of the reactive section by means of two pumps, one for water, the other for dimethyl adipate.

The methanol formed was obtained at the column head, whereas the water/adipic acid mixture was withdrawn at the base.

The resin was arranged in the reactive section of the column according to two types of packaging.

1. Packaging (a)

The resin was placed inside four pods, the walls of which were a metal gauze having a mesh of approximately 500 μm, less than the diameter of the beads of the resin.

These pods, 45 cm long, were sealed at their ends. They were maintained side by side by a metal fabric, in order to ensure the cohesion of the assembly and to promote liquid/vapor exchanges, as well as the redistribution of the liquid towards the pods containing the resin.

The amount of resin thus represented 26% of the volume of the reactive section of the column. The number of theoretical stages of this section was 4. Each theoretical stage contained 36.25 g of wet resin (containing 65% or 50% water according to the resin used).

2. Packaging (b)

The resin was arranged inside a sandwich defined by two layers of metal gauze having a mesh of approximately 500 μm. This sandwich, containing a thin resin layer, was folded "accordion-style" with an amplitude of the folds such that it packed the entirety of the cross-section of the column section.

Each sandwich thus folded had a height of 15 cm. Three were therefore necessary to pack the 45 cm of the reactive section of the column. Each sandwich, inside the column, was directed perpendicularly with respect to the preceding one, to avoid preferentially extending outside the regions charged with resin.

The amount of resin thus represented 32% of the volume of the reactive section of the column. The number of theoretical stages of this section was 4. Each theoretical stage contained 45 g of wet resin (containing 65% or 50% water according to the resin used).

These two types of packaging of the resin constitute a reactive packing permitting catalysis of the reaction and promoting liquid/vapor exchanges in order to conduct a separation by distillation.

EXAMPLES 1 AND 2

These two examples were carried out using a resin/gel A containing sulfonic acid groups, provided in the form of beads having a diameter of 1,000 μm and which had a level of divinylbenzene by weight with respect to the total weight of the skeleton based on styrene and divinylbenzene (or degree of crosslinking) of 4%, an exchange capacity of 5.4 milliequivalents (meq) $H^+/g$ and a moisture content of approximately 65%.

The two examples were carried out using the type (a) resin packaging described above.

The feed flow rates were the following:

| | |
|---|---|
| (i) dimethyl adipate (DMA): | 188 g/h (Example 1), 100 g/h (Example 2), |
| (ii) water: | 295 g/h (Example 1), 155 g/h (Example 2). |

The working pressure was equal to atmospheric pressure.

In continuous operation, the temperature at the column head was 65° C. (namely, the boiling temperature of pure methanol at atmospheric pressure). The temperature at the base was 101° C.

Analyses by HPLC (high performance liquid chromatography) enabled calculating the degree of conversion (DC) of the DMA, the yield (RY) of adipic acid (AA) expressed in mol % with respect to the DMA charged and the productivity of the reaction expressed in kg of AA per kg of dry resin per hour.

These results, as well as the conditions of operation, are reported in the Table below.

EXAMPLE 3 AND COMPARATIVE TEST 1

These two tests were carried out:

(1) one (Example 3) using the resin/gel described in Examples 1 and 2 (resin A), (2) the other (Comparative Test 1) using a macroporous resin B having a polystyrene/divinylbenzene skeleton and containing sulfonic acid groups but not having all of the characteristics of the invention: degree of crosslinking of 16%, exchange capacity of 5.4 meq $H^+/g$ of dry resin, beads having a diameter of 1,000 μm and a moisture content of approximately 50%, these two resins being employed in the type (b) packaging described above.

The reaction conditions of these tests were the same as for Examples 1 and 2, with the exception of the feed flow rates which were the following:

| (i) DMA: | 152 g/h |
|---|---|
| (ii) water: | 295 g/h |

The results obtained, as well as the conditions of operation, are reported in the Table below.

COMPARITIVE TEST 2

This test was carried out using resin A, in an amount equal to that employed in Example 3, but by arranging it in the distillation flask and not in the column. Thus, no reactive distillation occurred as in the process of the invention; rather, a continuous stirred reactor was used, surmounted by a column for removing the methanol formed.

The feed flow rates and the operating conditions were the same as in Example 3.

The results obtained, as well as the conditions of operation, are reported in the Table below.

EXAMPLE 4

This example was carried out using resin A, arranged in the type (b) packaging described above.

In order to obtain a higher AA yield than in the above examples, the column used contained a 99 cm reactive section with, in practice, 9 theoretical stages.

The feed flow rates and the operating conditions were the same as in Example 3.

The results obtained, as well as the conditions of operation, are reported in the Table below.

COMPARATIVE TEST 3

This test was carried out using resin B, arranged in the type (b) packaging described above.

In order to obtain a higher AA yield than in the above examples, the column used contained a 340 cm reactive section with 30 theoretical stages.

The feed flow rates and the operating conditions were the same as in Example 3.

The results obtained, as well as the conditions of operation, are reported in the Table below.

TABLE

| Tests | Resin | Flow rate in g/h | % by volume/volume of resin in the reactive section | DC (DMA) | RY (AA) | Productivity kg AA/kg dry resin/h |
|---|---|---|---|---|---|---|
| Example 1 | A | $H_2O$: 295 DMA: 188 | 26 | 99.0% | 80.4% | 2.486 |
| Example 2 | A | $H_2O$: 155 DMA: 100 | 26 | 99.97% | 93% | 1.543 |
| Example 3 | A | $H_2O$: 295 DMA: 152 | 32 | 99.95% | 92.7% | 1.886 |
| Example 4 | A | $H_2O$: 295 DMA: 152 | 32 | 99.95% | 97% | 0.877 |
| Comparative Test 1 | B | $H_2O$: 295 DMA: 152 | 32 | 96.5% | 61% | 1.249 |
| Comparative Test 2 | A | $H_2O$: 295 DMA: 152 | — | 97.1% | 82.6% | 1.677 |
| Comparative Test 3 | B | $H_2O$: 295 DMA: 152 | 32 | 99.95% | 97% | 0.179 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a dicarboxylic acid, comprising reactively distilling and hydrolyzing admixture of a $C_1$-$C_4$ alkyl aliphatic dicarboxylate and water, in liquid phase, in a distillation column, the lower end of which distillation column being charged with a gel of a crosslinked styrene/divinylbenzene resin bearing sulfonic acid substituents, the amount by weight of divinylbenzene comprising said resin ranging from 1% to 12% based on the total weight thereof and said resin having an exchange capacity of from 3 to 6.5 milliequivalents $H^+$/gram of dry resin, also comprising introducing said dicarboxylate/water admixture into the middle region of said column, withdrawing dicarboxylic acid from the base thereof and overhead distilling the alcohol of hydrolysis.

2. The process as defined by claim 1, said resin comprising particulates, the mean particle size of which ranging from 100 to 2,000 micrometers.

3. The process as defined by claim 2, said resin having a mean particle size ranging from 200 to 1,200 micrometers.

4. The process as defined by claim 1, said resin comprising from 2% to 5% by weight of divinylbenzene.

5. The process as defined by claim 1, said resin having ah exchange capacity of from 5 to 6.5 milliequivalents $H^+$/gram of dry resin.

6. The process as defined by claim 1, said dicarboxylate comprising a $C_1$-$C_4$ alkyl ester of a $C_3$-$C_6$ aliphatic dicarboxylic acid.

7. The process as defined by claim 6, said dicarboxylate comprising the methyl, ethyl or n-propyl esters of succinic, ethylsuccinic, glutaric, methylglutaric, adipic, 2-hexenedioic or 3-hexenedioic acids, or mixture thereof.

8. The process as defined by claim 6, said dicarboxylate comprising dimethyl adipate, dimethyl methylglutarate, dimethyl ethylsuccinate, a dimethyl hexenedioate, or mixture thereof.

9. The process as defined by claim 8, said dicarboxylate comprising dimethyl adipate.

10. The process as defined by claim 1, said dicarboxylate/water admixture being introduced into said column above the level of said resin.

11. The process as defined by claim 1, the amount of water in said dicarboxylate/water admixture being such that the water/dicarboxylate molar ratio is at least 2.

12. The process as defined by claim 11, said molar ratio ranging from 5 to 60.

13. The process as defined by claim 1, the temperature of hydrolysis ranging from 80° to 150° C.

14. The process as defined by claim 13, the temperature of hydrolysis ranging from 90° to 130° C.

* * * * *